United States Patent [19]

Cohen et al.

[11] Patent Number: 5,204,398

[45] Date of Patent: Apr. 20, 1993

[54] COMPOSITE DENTAL CEMENT COMPOSITION CONTAINING A LANTHANIDE SERIES COMPOUND

[75] Inventors: Brett I. Cohen, Nanuet; Douglas M. Achan, Glendale, both of N.Y.

[73] Assignee: Essential Dental Systems, Inc., South Hackensack, N.J.

[21] Appl. No.: 852,695

[22] Filed: Mar. 17, 1992

[51] Int. Cl.$^5$ ............................................. C08K 3/10
[52] U.S. Cl. .................................... 524/403; 524/430; 523/116
[58] Field of Search ................. 524/403, 430; 523/116

[56] References Cited

U.S. PATENT DOCUMENTS

| | | | |
|---|---|---|---|
| 3,911,581 | 10/1975 | Dietz | 32/15 |
| 3,971,754 | 7/1976 | Jurecic | 260/42 |
| 3,975,203 | 8/1976 | Dietz | 106/299 |
| 4,350,532 | 9/1982 | Randklev | 106/30 |
| 4,358,549 | 11/1982 | Randklev | 523/117 |
| 4,503,169 | 3/1985 | Randklev | 523/117 |
| 4,600,389 | 7/1986 | Schwartz | 433/217.1 |
| 4,650,847 | 3/1987 | Omura et al. | 526/376 |
| 4,714,721 | 12/1987 | Franek et al. | 523/113 |
| 4,882,392 | 11/1989 | Smid et al. | 525/328.6 |
| 4,927,856 | 5/1990 | Purrmann et al. | 523/115 |
| 5,034,433 | 7/1991 | Cohen et al. | 523/400 |
| 5,055,497 | 10/1991 | Okada et al. | 523/116 |

Primary Examiner—Thurman K. Page
Assistant Examiner—LaVonda R. DeWitt
Attorney, Agent, or Firm—Gottlieb, Rackman & Reisman

[57] ABSTRACT

A composite dental cement composition that is suitable for application with dental posts for either post insertion in a tooth or during core formation is provided. The cement composition includes a polymer matrix in an amount between about 15 and 50 weight percent, a filler in an amount between about 35 and 80 weight percent, and a lanthanide series compound in an amount between about 1 and 20 weight percent. The lanthanide series compound chemically interacts or pushes the air voids out between with the polymer matrix in order to increase compressive strength of the cement composition. Titanium powder may be added in order to increase compressive strength. A fluoride compound may further be added in order to substantially eliminate caries and further tooth decay.

43 Claims, No Drawings

COMPOSITE DENTAL CEMENT COMPOSITION CONTAINING A LANTHANIDE SERIES COMPOUND

BACKGROUND OF INVENTION

This invention relates to a restorative composite dental cement composition, and more particularly, to a dental cement composition having a substantially high compressive strength that is suitable for application with a dental post or as a core build-up material.

Dental restorative cement compositions have achieved wide commercial success and are extensively used in clinical dental practice. The leading U.S. patent on dental restorative cement compositions is U.S. Pat. No. 3,066,112 to Bowen, which describes a dental cement composition that consists of a liquid polymerizable organic resin matrix and finely divided inorganic filler materials.

As described in the Bowen patent, the liquid polymerizable organic resin matrix is typically prepared by combining bisphenol A-glycidyl methacrylate with one or more active monomers, preferably other methacrylates. As part of the system, a catalyst or initiator is used, such as benzoyl peroxide, along with a base or polymerization accelerator such as a toluidine compound. Other ingredients such as stabilizers, absorbents and pigments may be added to the composition.

Although the compositions described in the Bowen patent, as well as those described in subsequent patents and references, are somewhat satisfactory, a major disadvantage of most prior art composite dental cement compositions is that they have a compressive strength when applied which is far from adequate. The compressive strength of a restorative composite dental cement composition is important for enhancing the wearability of the restorative composition.

In U.S. Pat. No. 5,034,433 to Cohen et al., a dental cement is described that is suitable for application with dental posts for post insertion in a tooth or during core formation. The cement includes titanium powder which interacts with the polymer matrix for increasing compressive strength. While the cement is advantageous, it is nevertheless less than desirable since the titanium composite is dark colored.

Accordingly, it would be desirable to provide a restorative composite dental cement composition having a high compressive strength whose viscosity may be varied depending upon the desired dental application.

SUMMARY

Generally speaking, in accordance with the invention, a composite dental cement composition containing a lanthanide series compound is provided. The composite dental cement composition includes a polymer matrix in an amount of between about 15 and 50 weight percent, a filler in an amount of between about 35 and 80 weight percent and a lanthanide series compound in an amount between about 1 and 20 weight percent. The composite dental cement composition is suitable for use in connection with dental post insertion into a post-hole formed in a tooth after a root canal procedure. The cement composition may also be used in connection with core buildup after dental post affixation in the tooth.

The composite dental cement composition of the invention is prepared by combining a catalyst component and a base component. The catalyst component includes a catalyst, a least one epoxy monomer and a filler. In application, the catalyst and base components are combined, which causes a setting reaction to take place.

In preparing the inventive composite composition, a lanthanide series compound is added either to the catalyst component, base component, or both prior to combining the base and catalyst components. The addition of a lanthanide series compound substantially increases the compressive strength of the composition.

Titanium powder may also be added to the inventive composition.

Accordingly, it is an object of this invention to provide an improved composite dental cement composition which is suitable for application with a dental post.

Yet another object of the invention is to provide an improved dental cement composition which includes a lanthanide series compound for increasing compressive strength and overall wear of the composition.

Another object of the invention is to provide an improved composite dental cement composition which may either have a low viscosity or a high viscosity depending upon the desired application.

Yet a further object of the invention is provide an improved composite dental cement composition which is prepared by combining a catalyst component and a base component.

It is still another object of the invention to provide an improved composite dental cement composition in which the epoxy monomer of the catalyst component and the epoxy monomer of the base component undergo extensive polymerization.

A further object of the invention is to provide an improved composite dental cement composition which includes a fluoride compound to substantially eliminate root caries and further tooth decay.

Still other objects and advantages of the invention will in part be obvious and will in part be apparent from the following description.

The invention accordingly comprises the several steps and the relation of one or more of the steps with respect to each of the others, and the composition or compositions having the features, properties, and a relation of constituents which are exemplified in the following detailed disclosure, and the scope of the invention will be indicated in the claims.

DETAILED DESCRIPTION OF THE PREFERRED EMBODIMENTS

The composite dental cement composition of the invention includes a polymer matrix in an amount between about 15 and 50 weight percent. Preferably, the polymer matrix comprises an epoxy matrix, and even more preferably an acrylic matrix. The acrylic matrix is formed from monomers of acrylates and methacrylates, such as di-, tri- and tetracrylates and methacrylates.

Suitable monomers of diacrylates include ethylene glycol diacrylate, diethylene glycol diacrylate, 1,4-dimethylolcyclohexane diacrylate and $C_2$–$C_{12}$ alkylene diacrylates.

Suitable monomers of dimethacrylate include bisphenol A-glycidyl methacrylate (BIS-GMA), triethylene glycol dimethacrylate, tetraethylene glycol dimethacrylate, ethylene glycol dimethacrylate, diethylene glycol dimethacrylate, butanediol dimethacrylate, hexanediolethylene dimethacrylate, neopentylglycol dimethacrylate, isobisphenol A-glycidyl methacrylate, trimethylolpropane dimethylacrylate, bisphenol A-ethoxylated dimethacrylate and bisphenol A-dimethacrylate. The preferred monomer of dimethacrylate is bisphenol A-glycidylmethacrylate (BIS-GMA) and is present in an amount between about 5 and 50 weight percent based on the total weight of the cement composition.

Suitable monomers of triacrylates and trimethacrylates include trimethylolpropane triacrylate, tetramethylolmethane triacrylate, tetramethylolmethane trimethylacrylate, trimethylolethane trimethacrylate and trimethylolpropane trimethacrylate.

Suitable monomers of tetracrylates and tetramethacrylates include tetramethylolmethane tetracrylate and tetramethylolmethane tetramethacrylate.

The purpose of the polymer matrix, specifically the acrylic matrix formed from monomers of acrylates and methacrylates, is to provide a binding network for the filler to be incorporated, thereby providing strength to the composite cement composition.

The filler of the inventive composite cement composition is selected from the group including quartz, silicon dioxide, fumed silicon dioxide, aluminum dioxide, titanium dioxide, zirconium dioxide, silicas, glass, graphite fibers, boron fibers, barium glass, alumino silicates, boro silicate glass, glass powders, hydroxyapatite, wood, micas and asbestos. The function of the filler ingredient is to be incorporated with the polymer matrix for adding strength to the overall inventive composition.

The lanthanide series compound is present in the inventive composition in an amount between about 1 and 20 weight percent.

The lanthanide series component comprises a powder and may be a pure metal, an oxide, a carbonate, a nitrate, a chloride, as well other salts. Suitable lanthanide series compounds include europium, lanthanum, cerium, neodymium, praseodymium, yttrium, gadolinium, samarium, terbium, dysprosium, holmium, erbium, thulium, ytterbium, and lutetium. The lanthanide powder is preferably 5-10 microns in size with a minimum purity of 98%. The preferred lanthanide powder comprises a mixture of the four lanthanides praseodymium, lanthanum, cerium and neodymium carbonate.

At least some of the lanthanide series component of the inventive composite dental cement may be chemically treated, and more preferably silanated using a silane compound selected from the group including gammamethacryloxy propyltrimethoxysilane (A-174), gammamethacryloxy propyltris(2-methoxyethoxy) silane (A-175), vinyl trichlorosilane, vinyl triethoxysilane, vinyl trimethoxysilane and vinyl triacetoxysilane.

Titanium powder may also be added to the inventive dental cement composition in an amount up to about 15 weight percent, preferably in an amount between about 2 and 10 weight percent. The titanium powder has a particle size of between 1 and 30 microns and a purity of at least 98%. At least some of the titanium powder may be chemically treated in a manner similar to treating the lanthanide series component as described hereinabove.

In Example 1 found below, the silanation of lanthanide (or titanium) powder is described.

EXAMPLE 1

25.15 grams of a lanthanide series powder (white) or titanium powder (black) was placed in a 50 ml screw cap vile. Then, 0.5 ml (0.51 gram) of gamma methacryloxypropyltrimethoxysilane (A-174) was added by use of a syringe, after which the syringe was washed with 3 ml of cyclohexane. Then, 1.4 ml of N-propylamine (1.04 grams) was added to the mixture also by syringe followed by 3 ml of an additional amount of cyclohexane in order to form a white or black-like suspension. The suspension was mixed for one and one half hours, after which the mixture was allowed to evaporate for approximately 24 hours. After 24 hours of evaporation, the remaining white or black powder was transferred to a 100 ml beaker where it was washed three times with 30 ml of cyclohexane. The purpose of the washing was to remove any soluble silane by-products and any residual N-propylamine. Thereafter, the resulting white or black powder was then allowed to air dry for an additional 24 hours after which 24.69 grams of a white or black powder was recovered (98% weight recovery). The resulting solid was found to be hydrophobic to water, illustrating that the lanthanide series powder or titanium powder had been silanated.

As shown in Example 1, the preferred silane for chemically treating the lanthanide and titanium ingredients of the inventive composite dental cement composition is gammamethacryloxypropyltrimethoxysilane (A-174).

The purpose of chemically treating the lanthanide and titanium ingredients is to chemically interact with the polymer matrix, thereby forming a copolymer-like lanthanide or titanium polymer matrix.

Although the inventive dental cement composite composition contains a lanthanide series compound in an amount between 1 and 2 weight percent, it is preferred that the lanthanide series compound is present in an amount between 2 and 10 weight percent based on the total weight of the composition.

Optionally, a fluoride compound may be added to the inventive composite dental cement composition in an amount between 0.5 and 6 weight percent. The purpose of the fluoride compound is to substantially eliminate root caries and further tooth decay. The fluoride compound is chosen from the group including sodium fluoride, tin fluoride, ytterbium fluoride, fluoride chosen from amine fluorides and fluorides chosen from acidulated phosphate fluorides.

In order to prepare the composite dental cement of the composition, a catalyst component and a base component are mixed together, which causes a chemical setting reaction. Particularly, the catalyst component includes a catalyst or polymerization initiator in an amount between about 0.2 and 2.0 weight percent, at least one epoxy monomer in an amount between 15 and 50 weight percent and a filler in an amount between about 40 and 80 weight percent.

The catalyst of the catalyst component is typically a free radical source, and more preferably an organic peroxide. Suitable organic peroxides include benzoyl peroxide, acetyl peroxide, parachlorobenzoyl peroxide, cumyl peroxide, t-butyl peroxide, lauroyl peroxide, t-butyl hydroperoxide, methylethyl ketone peroxides, t-butyl peroxybenzoate, 2,5-dimetylhexane, 2,5-dihydroperoxide and t-cumyl hydroperoxide. Benzoyl peroxide is the most preferred catalyst for the catalyst component.

The base component which is used for preparing the composite dental cement composition includes a base or accelerator in an amount between about 0.2 and 1.5 weight percent, at least one epoxy monomer in an amount between about 20 and 50 weight percent and a filler in an amount between about 45 and 85 weight percent. Preferably, the base of the base component is an amine compound chosen from amines such as propylamine, N-butylamine, pentylamine, hexylamine, dimethylamine, diethylamine, dipropylamine, di-n-butylamine, dipentylamine, trimethylamine, triethylamine, tripropylamine, tri-n-butylamine, tripentylamine, 4-methylaniline, N-N-bis-(2-hydroxyethyl)-3,5-dimethylaniline, N-methyl-N(2-hydroxyethyl)-4-methylaniline and long chain fatty amines such as NN' dimethylaniline and N-methyldiphenylamine. Diamines can also be used such as ethylene diamine, trimethylene diamine, tetramethylene diamine, pentamethylene diamine and hexamethylene diamine.

As will be shown in the examples hereinbelow, the preferred amine is NN' dihydroxyethyl-p-toluidine. Other toluidines may be used such as N,N-dimethyl-p-toluidine and N,N-diethyl-p-toluidine.

For either the catalyst or base components, the epoxy monomer is chosen preferably from monomers of methacrylate, as described hereinabove.

When the catalyst and base components are combined, a chemical setting reaction takes place which will last on the average of three to five minutes in order to fully set the inventive composite dental cement composition.

When combining the catalyst and base components, the lanthanide series compound is added. The lanthanide series compound may be added either to the catalyst or base component, or to both, prior to combining the two components. Alternatively, the lanthanide series compound may be added to the base and catalyst components immediately after they are combined. Preferably, the lanthanide series compound should be added to the base and catalyst prior to combining the two components. This insures the proper wetting of the lanthanide series powder.

Preferably, substantially equal amounts of catalyst component and base component are combined in order to form the inventive composite dental cement composition. Once the catalyst and base components are combined, the peroxide compound contained in the catalyst component is fully initiated when brought into contact with the amine compound (free radicals are formed) found in the base component. As a result, substantial polymerization of the acrylic monomers takes place, resulting in a strong polymer matrix of the inventive composite dental cement composition.

A lanthanide series compound is added to the inventive composite dental cement composition in order to interact with the polymer matrix (to push out air voids or to form a copolymerlike composition) for increasing compressive strength of the resulting composition, and for increasing wear of the overall inventive composition. In particular, the lanthanide series compound is added in order to push out the air voids found between the matrices. Chemically modified lanthanide series powder chemically interacts with the polymer matrix, resulting in increased compressive strength. However, as demonstrated in the examples in this application, unmodified lanthanide series powder is more effective at increasing the compressive strength of the composition than chemically modified (silanated) lanthanide series powder.

Additionally, reduction of the coefficient of thermal expansion may be associated with the inventive composition. Other ingredients, such as stabilizers and absorbents, may be present to increase shelf life and prevent degradation of properties. Also, various dyes or pigments may be added to obtain various color shades for conforming to the tooth color to which the inventive composition is applied.

The composite dental cement containing a lanthanide series compound (without titanium powder) of the invention may be colored with a metal oxide. Suitable metals for the metal oxide include titanium (producing a white colored oxide), iron (producing either a red or black colored oxide), cadmium or iron (producing a yellow colored oxide) and chromium or iron (producing a brown colored oxide). Any combination may be used to produce a variety of tooth color shades. The metal oxide colorants may be added in an amount between about 0.005 and 0.5 weight percent.

In order to better comprehend the inventive composite dental cement composition, the following examples are provided. In each example, a substantially equal amount of the base and catalyst components were mixed for approximately 30 seconds in order to initiate a chemical setting reaction, resulting in the formation of the inventive composite dental cement composition.

EXAMPLE 2 (CONTROL)

| Catalyst Formulation | |
|---|---|
| 5u quartz silanized | 57.185 weight percent (57.185 grams) |
| BIS-GMA | 26.9745 weight percent (26.9745 grams) |
| Triethylene glycol dimethacrylate with BHT | 10.601 weight percent (10.601 grams) |
| Aluminum oxide C | 2.4586 weight percent (2.4586 grams) |
| Cabosil M-5 | 1.2293 weight percent (1.2293 grams) |
| Benzoyl peroxide | 0.9017 weight percent (0.9017 gram) |
| Aerosil R-972 | 0.6147 weight percent (0.6147 gram) |
| BHT | 0.03514 weight percent (0.03514 gram) |
| Base Formulation | |
| Ground kimble glass silanized | 35.808 weight percent (35.808 grams) |
| 5u quartz silanized | 23.625 weight percent (23.625 grams) |
| BIS-GMA | 18.144 weight percent (18.144 grams) |
| Ethoxylated bisphenol A-dimethacrylate with BHT | 12.096 weight percent (12.096 grams) |
| 1,6 hexamethylene dimethacrylate | 5.040 weight percent (5.040 grams) |
| Triethylene glycol dimethacrylate with MEHQ | 4.0915 weight percent (4.0915 grams) |
| NN' dihydroxyethyl-p-toluidine | 0.4900 weight percent (0.49000 gram) |
| Uvinul 400 | 0.3578 weight percent (03578 gram) |
| Aerosil R-972 | 0.2387 weight percent (0.2387 gram) |
| Bisphenol A-dimethacrylate | 0.1008 weight percent (0.1008 gram) |
| Titanium dioxide | 0.006 weight percent (0.006 gram) |
| Tint concentrate | 0.002057 weight percent (0.002057 gram) |

In order to prepare the catalyst components, 10.601 grams of triethylene glycol dimethacrylate with BHT (butylated hydroxytoluene), 0.03514 gram of BHT and 0.9017 gram of benzoyl peroxide were mixed until the BHT and benzoyl peroxide reagents were fully dissolved in the triethylene glycol dimethacrylate. Then, warm BIS-GMA (26.9745 grams) was added to the above mixture and stirred until the resulting mixture was a homogenous solution. Then, aerosil R-972 (0.6147 gram), cabosil M-5 (1.2293 grams)(amorphous fumed silica), aluminum oxide C (2.4586 grams) and 5 u quartz silanized (57.185 grams) were blended together (mixed for 10 mins) and then added to the resulting resin mixture. This resulted in approximately 100 grams of the catalyst component portion of the composition.

In order to prepare the base component, 5.040 grams of 1,6 hexamethylene dimethacrylate, 4.0915 grams of triethylene glycol dimethacrylate with MEHQ (4-methoxyphenol), 0.3578 grams of uvinul 400 (2,4 dihydroxy benzophenone), 0.1008 grams of bisphenol A-dimethacrylate, and 0.4900 grams of NN'dihydroxyethyl-p-toluidine were all mixed together until a homogenous solution resulted. Then, 12.096 grams of ethyoxylated bisphenol A-dimethacrylate with BHT in warm BIS-GMA (16.144 grams) were added to the above solution until a second homogenous solution resulted. Then, tint concentrate (0.002057 grams), titanium dioxide (0.006 grams), aerosil R-972 (0.2387 grams), 5 u quartz silanized (23.625 grams), and ground kimble glass silanized (35.808 grams) were all mixed together to give a white powder mixture. This white powder mixture was then mixed with the BIS-GMA resin solution that was mixed before and approximately 100 grams of the base portion of the composition was obtained.

Then, equal weights of the base and catalyst (5 grams/5 grams) components were mixed for 30 seconds. This mixing produced a setting reaction which lasted for about 3-5 minutes. As a result, a composite dental cement is formed having a compressive strength after placed for 24 hours in water of 29534 psi.

EXAMPLE 3

Equal amounts of the base component (5 grams) and the catalyst component (5 grams) described in Example 2 were mixed. Immediately thereafter, chemically treated lanthanum oxide powder (2.5 grams) was added to the mixture of base and catalyst components and mixed for 30 seconds, producing a white material. This mixing caused a setting reaction which lasted for about 3-5 minutes. As a result, a composite dental cement was formed having a compressive strength after placed for 24 hours in water of 46248 psi.

EXAMPLE 4

Equal amounts of the base component (5 grams) and the catalyst component (5 grams) described in Example 2 were mixed. Immediately thereafter, non-chemically treated lanthanium oxide powder (1.11 grams) was added to the mixture of base and catalyst components and mixed for thirty seconds, producing a white material. This mixing caused a setting reaction which lasted for about 3-5 minutes. As a result, a composite dental cement was formed having a compressive strength after placed for 24 hours in water of 52452 psi.

EXAMPLE 5

Equal amounts of the base component (5 grams) and the catalyst component (5 grams) described in Example 2 were mixed. Immediately thereafter, non-chemically treated praseodymium, lanthanum, cerium and neodymium carbonate powder (0.638 gram) was added to the mixture of base and catalyst components and mixed for 30 seconds, producing a white material. This mixing caused a setting reaction to take place which lasted for about 3-5 minutes. As a result, a composite dental cement composition was formed having a compressive strength after placed for 24 hours in water of 54415 psi.

EXAMPLE 6

Equal amounts of the base component (5 grams) and the catalyst component (5 grams) described in Example 2 were mixed. Immediately thereafter, non-chemically treated praseodymium, lanthanum, cerium and neodymium carbonate powder (0.666 gram) and sodium fluoride (0.444 gram) were added to the mixture of base and catalyst components and mixed for 30 seconds, producing a white material. This mixing caused a setting reaction to take place which lasted for about 3-5 minutes. As a result, a composite dental cement was formed having a compressive strength after placed for 24 hours in water of 50578 psi.

EXAMPLE 7

Equal amounts of the base component (5 grams) and the catalyst component (5 grams) described in Example 2 were mixed. Immediately thereafter, non-chemically treated lanthanum oxide powder (0.6736 gram) and sodium fluoride powder (0.5613 gram) were added to the mixture of base and catalyst components and mixed for 30 seconds, producing a white material. This mixing caused a setting reaction which lasted for about 3-5 minutes. As a result, a composite dental cement composition was formed having a compressive strength after placed for 24 hours in water of 58712 psi.

EXAMPLE 8

Equal amounts of the base component (5 grams) and the catalyst component (5 grams) described in Example 2 were mixed. Immediately thereafter, non-chemically treated praseodymium, lanthanum, cerium and neodymium carbonate powder (0.6736 gram) and chemically treated titanium powder (0.5613 gram) were added to the mixture of base and catalyst components and mixed for about 30 seconds, producing a light gray material. This mixing caused a setting reaction to take place which lasted for about 3-5 minutes. As a result, a composite dental cement was formed having a compressive strength after placed for 24 hours in water of 54178 psi.

EXAMPLE 9

Equal amounts of the base component (5 grams) and the catalyst component (5 grams) described in Example 2 were mixed. Immediately thereafter, non-chemically treated praseodymium, lanthanum, cerium and neodymium carbonate powder (0.6896 gram), non-chemically treated titanium powder (0.3448 gram) and sodium fluoride (0.4597 gram) were added to the mixture of base and catalyst components and mixed for 30 seconds, producing a light gray material. This mixing caused a setting reaction to take place which lasted for about 3-5 minutes. As a result, a composite dental cement was formed having a compressive strength after placed for 24 hours in water of 56692 psi.

EXAMPLE 10 (CONTROL)

| Catalyst Formulation | |
| --- | --- |
| 5u quartz silanized | 8.18 weight percent (8.18 grams) |
| 325 m quartz silanized | 66.43 weight percent (66.43 grams) |

| -continued | |
|---|---|
| BIS-GMA | 5.11 weight percent (5.11 grams) |
| Triethylene glycol dimethacrylate with MEHQ | 16.6 weight percent (16.6 grams) |
| Aluminum oxide C | 3.066 weight percent (3.066 grams) |
| Benzoyl peroxide | 0.5826 weight percent (0.5826 gram) |
| BHT | 0.0254 weight percent (0.0254 gram) |
| Base Formulation | |
| 325 m quartz silanized | 53.1 weight percent (53.1 grams) |
| 5u quartz silanized | 16.65 weight percent (16.65 grams) |
| BIS-GMA | 13.03 weight percent (13.03 grams) |
| Ethoxylated bisphenol A-dimethacrylate | 8.69 weight percent (8.69 grams) |
| 1,6 hexamethylene dimethacrylate with MEHQ | 3.618 weight percent (3.618 grams) |
| Triethylene glycol dimethacrylate with MEHQ | 2.898 weight percent (2.896 grams) |
| NN' dihydroxyethyl-p-toluidine | 0.3618 weight percent (0.3618 gram) |
| Uvinul 400 | 0.261 weight percent (0.261 gram) |
| Titanium dioxide | 0.778 weight percent (0.778 gram) |
| Cabosil M-5 | 0.605 weight percent (0.605 gram) |
| MEHQ | 0.00534 weight percent (0.00534 gram) |

In order to prepare the catalyst component, 16.6 grams of triethylene glycol dimethacrylate with MEHQ, 0.0254 gram of BHT and 0.5826 gram of benzoyl peroxide were added together until the BHT and benzoyl peroxide reagents were fully dissolved in the triethylene glycol dimethacrylate. Then, warm BIS-GMA (5.11 grams) was added and stirred to give a homogenous mixture. Then, a blended mixture of the following powders: aluminum oxide C (3.066 grams), 5 u quartz silanized (8.18 grams) and 325 m quartz silanized powder (66.43 grams) was added to the resin mixture. This resulted in approximately 100 grams of the catalyst component of the composition.

In order to prepare the base component, 1,6-hexamethylene dimethacrylate with MEHQ (3.618 grams), triethylene glycol dimethacrylate with MEHQ (2.898 grams), MEHQ (0.00534 gram), uvinul 400 (0.261 gram), and NN' dihydroxyethyl-p-toluidine (0.3618 gram) were all mixed together to form a homogenous solution. Then, ethoxylated bisphenol A-dimethacrylate (8.69 grams) was added to produce a second homogenous solution after complete mixing. Then, warm BIS-GMA resin (13.03 grams) was added and stirred until a homogenous mixture also developed. Then, the following solids were blended together: titanium dioxide (0.778 gram), cabosil M-5 (0.605 gram), 5 u quartz silanized (16.65 grams) and 325 m quartz silanized (53.1 grams). This blended mixture of powders was added to the BIS-GMA resin mixture prepared before to yield approximately 100 grams of the base component of the composition.

EXAMPLE 11

Equal amounts of the base component (5 grams) and the catalyst component (5 grams) described in Example 10 were mixed. Immediately thereafter, chemically treated praseodymium, lanthanum, cerium and neodymium carbonate powder (1.11 grams) was added to the mixture of base and catalyst components and mixed for 30 seconds, producing a white material. This mixing caused a setting reaction to take place which lasted for about 3-5 minutes. As a result, a composite dental cement composition was formed having a compressive strength after placed for 24 hours in water of 38541 psi.

EXAMPLE 12

Equal amounts of the base component (5 grams) and the catalyst component (5 grams) described in Example 10 were mixed. Immediately thereafter, chemically treated praseodymium, lanthanum, cerium and neodymium carbonate powder (1.764 grams) was added to the mixture of base and catalyst components and mixed for 30 seconds, producing a white material. This mixing caused a setting reaction to take place which lasted for about 3-5 minutes. As a result, a composite dental cement composition was formed having a compressive strength after placed for 24 hours in water of 39282 psi.

EXAMPLE 13

Equal amounts of the base component (5 grams) and the catalyst component (5 grams) described in Example 10 were mixed. Immediately thereafter, chemically treated praseodymium, lanthanum, cerium and neodymium carbonate powder (2.5 grams) was added to the mixture of base and catalyst components and mixed for 30 seconds, producing a white material. This mixing caused a setting reaction to take place which lasted for about 3-5 minutes. As a result, a composite dental cement composition was formed having a compressive strength after placed for 24 hours in water of 34632 psi.

EXAMPLE 14

Equal amounts of the base component (5 grams) and the catalyst component (5 grams) described in Example 10 were mixed. Immediately thereafter, non-chemically treated praseodymium, lanthanum cerium and neodymium carbonate powder (1.11 grams) was added to the mixture of base and catalyst components and mixed for 30 seconds, producing a white material. This mixing caused a setting reaction to take place which lasted for about 3-5 minutes. As a result, a composite dental cement composition was formed having a compressive strength after placed for 24 hours in water of 43413 psi.

EXAMPLE 15

Equal amounts of the base component (5 grams) and the catalyst component (5 grams) described in Example 10 were mixed. Immediately thereafter, non-chemically treated praseodymium, lanthanum, cerium and neodymium carbonate powder (1.764 grams) was added to the mixture of base and catalyst components and mixed for 30 seconds, producing a white material. This mixing caused a setting reaction to take place which lasted for about 3-5 minutes. As a result, a composite dental cement composition was formed having a compressive strength after placed for 24 hours in water of 41536 psi.

EXAMPLE 16

Equal amounts of the base component (5 grams) and the catalyst component (5 grams) described in Example 10 were mixed. Immediately thereafter, non-chemically treated praseodymium, lanthanum, cerium and neodymium carbonate powder (2.5 grams) was added to the mixture of base and catalyst components and mixed for 30 seconds, producing a white material. This mixing caused a setting reaction to take place which lasted for about 3-5 minutes. As a result, a composite dental cement composition was formed having a compressive strength after placed for 24 hours in water of 40055 psi.

EXAMPLE 17

Equal amounts of the base component (5 grams) and the catalyst component (5 grams) described in Example 10 were mixed. Immediately thereafter, non-chemically treated lanthanum oxide powder (0.309 grams) was added to the mixture of base and catalyst components and mixed for 30 seconds, producing a white material. This mixing caused a setting reaction to take place which lasted for about 3-5 minutes. As a result, a composite dental cement composition was formed having a compressive strength after placed for 24 hours in water of 45454 psi.

EXAMPLE 18

Equal amounts of the base component (5 grams) and the catalyst component (5 grams) described in Example 2 were mixed. Immediately thereafter, non-chemically treated praseodymium, lanthanum, cerium and neodymium carbonate powder (0.309 grams) was added to the mixture of base and catalyst components and mixed for 30 seconds, producing a white material. This mixing caused a setting reaction to take place which lasted for about 3-5 minutes. As a result, a composite dental cement composition was formed having a compressive strength after placed for 24 hours in water of 46157 psi.

EXAMPLE 19

Equal amounts of the base component (5 grams) and the catalyst components (5 grams) described in Example 10 were mixed. Immediately thereafter, non-chemically treated praseodymium, lanthanum, cerium and neodymium carbonate powder (0.43 gram) and sodium fluoride (0.323 gram) were added to the mixture of base and catalyst components and mixed for 30 seconds, producing a white material. This mixing caused a setting reaction to take place which lasted for about 3-5 minutes. As a result, a composite dental cement composition was formed having a compressive strength after placed for 24 hours in water of 46655 psi.

EXAMPLE 20

Equal amounts of the base component (5 grams) and the catalyst component (5 grams) described in Example 10 were mixed. Immediately thereafter, non-chemically treated praseodymium, lanthanum, cerium and neodymium carbonate powder (0.4395 gram) and sodium fluoride (0.5494 gram) were added to the mixture of base and catalyst components and mixed for 30 seconds, producing a white material. This mixing caused a setting reaction to take place which lasted for about 3-5 minutes. As a result, a composite dental cement composition was formed having a compressive strength after placed for 24 hours in water of 45759 psi.

EXAMPLE 21

Equal amounts of the base component (5 grams) and the catalyst component (5 grams) described in Example 10 were mixed. Immediately thereafter, non-chemically treated praseodymium, lanthanum, cerium and neodymium carbonate powder (0.4210 gram) and non-chemically treated titanium powder (0.1052 gram) were added to the mixture of base and catalyst components and mixed for 30 seconds, producing a light grey material. This mixing caused a setting reaction to take place which lasted for about 3-5 minutes. As a result, a composite dental cement composition was formed having a compressive strength after placed for 24 hours in water of 4359 psi.

EXAMPLE 22

Equal amounts of the base component (5 grams) and the catalyst components (5 grams) described in Example 10 were mixed. Immediately thereafter, non-chemically treated lanthanum oxide powder (0.4395 gram) and non-chemically treated titanium powder (0.5494 gram) were added to the mixture of base and catalyst components and mixed for 30 seconds, producing a light grey material. This mixing caused a setting reaction to take place which lasted for about 3-5 minutes. As a result, a composite dental cement composition was formed having a compressive strength after placed for 24 hours in water of 42920 psi.

EXAMPLE 23

Equal amounts of the base component (5 grams) and the catalyst component (5 grams) described in Example 10 were mixed. Immediately thereafter, non-chemically treated lanthanum oxide powder (0.4210 gram) and chemically treated titanium powder (0.1052 gram) were added to the mixture of base and catalyst components and mixed for 30 seconds, producing a light grey material. This mixing caused a setting reaction to take place which lasted for about 3-5 minutes. As a result, a composite dental cement composition was formed having a compressive strength after placed for 24 hours in water of 43296 psi.

EXAMPLE 24

Equal amounts of the base component (5 grams) and the catalyst component (5 grams) described in Example 10 were mixed. Immediately thereafter, non-chemically treated praseodymium, lanthanum, cerium and neodymium carbonate powder (0.4347 gram) and chemically treated titanium powder (0.4347 gram) were added to the mixture of base and catalyst components and mixed for 30 seconds, producing a light grey material. This mixing caused a setting reaction to take place which lasted for about 3-5 minutes. As a result, a composite dental cement composition was formed having a compressive strength after placed for 24 hours in water of 46204 psi.

EXAMPLE 25

Equal amounts of the base component (5 grams) and the catalyst component (5 grams) described in Example 10 were mixed. Immediately thereafter, non-chemically treated cerium oxide powder (0.4210 gram) and chemically treated titanium powder (0.1052 gram) were added to the mixture of base and catalyst components and mixed for 30 seconds, producing a light grey material. This mixing caused a setting reaction to take place which lasted for about 3-5 minutes. As a result, a composite dental cement composition was formed having a compressive strength after placed for 24 hours in water of 45969 psi.

EXAMPLE 26

Equal amounts of the base component (5 grams) and the catalyst component (5 grams) described in Example 10 were mixed. Immediately thereafter, non-chemically treated neodymium oxide powder (0.4395 gram) and chemically treated titanium powder (0.5494 gram) were added to the mixture of base and catalyst components and mixed for 30 seconds, producing a light grey material. This mixing caused a setting reaction to take place which lasted for about 3-5 minutes. As a result, a composite dental cement composition was formed having a compressive strength after placed for 24 hours in water of 41168 psi.

EXAMPLE 27

Equal amounts of the base component (5 grams) and the catalyst component (5 grams) described in Example 10 were mixed. Immediately thereafter, non-chemically treated praseodymium, lanthanum, cerium and neodymium carbonate powder (0.465 gram) and chemically treated titanium powder (1.163 grams) were added to the mixture of base and catalyst components and mixed for 30 seconds, producing a light grey material. This mixing caused a setting reaction to take place which lasted for about 3-5 minutes. As a result, a composite dental cement composition was formed having a compressive strength after placed for 24 hours in water of 39904 psi.

EXAMPLE 28

Equal amounts of the base component (5 grams) and the catalyst component (5 grams) described in Example 10 were mixed. Immediately thereafter, non-chemically treated cerium oxide powder (0.4210 gram) and non-chemically treated titanium powder (0.105 gram) were added to the mixture of base and catalyst components and mixed for 30 seconds, producing a light material. This mixing caused a setting reaction to take place which lasted for about 3-5 minutes. As a result, a composite dental cement composition was formed having a compressive strength after placed for 24 hours in water of 50503 psi.

EXAMPLE 29

Equal amounts of the base component (5 grams) and the catalyst component (5 grams) described in Example 10 were mixed. Immediately thereafter, non-chemically treated praseodymium, lanthanum, cerium and neodymium carbonate powder (0.4254 gram) and non-chemically treated titanium powder (0.2127 gram) were added to the mixture of base and catalyst components and mixed for 30 seconds, producing a light grey material. This mixing caused a setting reaction to take place which lasted for about 3-5 minutes. As a result, a composite dental cement composition was formed having a compressive strength after placed for 24 hours in water of 58004 psi.

EXAMPLE 30

Equal amounts of the base component (5 grams) and the catalyst component (5 grams) described in Example 10 were mixed. Immediately thereafter, non-chemically treated cerium oxide powder (0.4395 gram) and non-chemically treated titanium powder (0.5494 gram) were added to the mixture of base and catalyst components and mixed for 30 seconds, producing a light grey material. This mixing caused a setting reaction to take place which lasted for about 3-5 minutes. As a result, a composite dental cement composition was formed having a compressive strength after placed for 24 hours in water of 46985 psi.

EXAMPLE 31

Equal amounts of the base component (5 grams) and the catalyst component (5 grams) described in Example 10 were mixed. Immediately thereafter, non-chemically treated praseodymium, lanthanum, cerium and neodymium carbonate powder (0.4545 gram), chemically treated titanium powder (0.4545 gram) and sodium fluoride (0.4545 gram) were added to the mixture of base and catalyst components and mixed for 30 seconds, producing a light grey material. This mixing caused a setting reaction to take place which lasted for about 3-5 minutes. As a result, a composite dental cement composition was formed having a compressive strength after placed for 24 hours in water of 47933 psi.

EXAMPLE 32

Equal amounts of the base component (5 grams) and the catalyst components (5 grams) described in Example 10 were mixed. Immediately thereafter, non-chemically treated praseodymium, lanthanum, cerium and neodymium carbonate powder (0.4395 gram), non-chemically treated titanium powder (0.2197 gram) and sodium fluoride (0.3296 gram) were added to the mixture of base and catalyst components and mixed for 30 seconds, producing a light grey material. This mixing caused a setting reaction to take place which lasted for about 3-5 minutes. As a result, a composite dental cement composition was formed having a compressive strength after placed for 24 hours in water of 49297 psi.

Examples 2-9 represent a low viscosity composite dental cement suitable for application with dental post insertion, while Examples 10-32 represent a high viscosity dental cement suitable for application during core build-up.

In order to better appreciate the inventive composite dental cement composition, the following Table is provided to illustrate how the addition of lanthanide(s) and titanium to the composition substantially increases the compressive strength thereof.

TABLE I

| Example | Compressive Strength (psi)* (after 24 hrs in water) | SD |
| --- | --- | --- |
| 2-control | 29534 | ±4352 |
| 3 | 46248 | ±4840 |
| 4 | 52452 | ±8209 |
| 5 | 54415 | ±8584 |
| 6 | 50578 | ±8771 |
| 7 | 58712 | ±7157 |
| 8 | 54178 | ±6459 |
| 9 | 56692 | ±7667 |
| 10-control | 23154 | ±3397 |
| 11 | 38541 | ±6400 |
| 12 | 39282 | ±5762 |
| 13 | 34632 | ±5857 |
| 14 | 43413 | ±3612 |
| 15 | 41536 | ±2726 |
| 16 | 40055 | ±4536 |
| 17 | 45454 | ±3060 |
| 18 | 46157 | ±2833 |
| 19 | 46655 | ±3440 |
| 20 | 45759 | ±4158 |
| 21 | 43592 | ±5643 |
| 22 | 42920 | ±4562 |
| 23 | 43296 | ±2344 |
| 24 | 46204 | ±6189 |
| 25 | 45969 | ±6057 |
| 26 | 41168 | ±3828 |
| 27 | 39904 | ±4218 |
| 28 | 50503 | ±6502 |
| 29 | 58004 | ±9642 |
| 30 | 46985 | ±5942 |

TABLE I-continued

| Example | Compressive Strength (psi)* (after 24 hrs in water) | SD |
|---|---|---|
| 31 | 47933 | ±6529 |
| 32 | 49297 | ±5453 |

*psi = pounds/square inch

The lanthanide series powder for the inventive composite cement was either silanated (chemically modified) or not chemically treated at all for incorporation chemically with the BIS-GMA (polymer) matrix. When unmodified or untreated lanthanide series powder is added and, as a result, the air is pushed out between matrices, the resulting composite cement is generally stronger as compared to a chemically modified lanthanide composite cement The compressive strength was measured after the composites were made into cylinders (for each Example, a minimum of ten samples were tested) and placed into water for 24 hours. These cylinders had an average diameter of 0.185 inches with an average height of 0.359 inches. The compressive strength was calculated from the following equation: $P/\pi \cdot r^2$ where P=pounds of force (load) and r=radius of the sample. A force that was applied at a cross head speed of 0.25 inches per minute (0.635 cm/min) resulted in samples that failed or samples that were crushed.

The composition in control Example 2 had a low viscosity and is suitable to cement posts into root canals. When silanated lanthanum oxide was added in Example 3, the compressive strength increased from 29534 psi to 46248 psi, a percent increase of 57%. In Example 4, half the amount of unmodified lanthanum oxide was added, and the compressive strength increased even further to 52452 psi, a percent increase of 78%.

In Example 5, an unmodified powdered mixture of praseodymium, lanthanum, cerium and neodymium carbonate was added, increasing the compressive strength to 54415 psi. In Example 6, when sodium fluoride was added as well, the compressive strength went down slightly to 50578 psi, but was still significantly greater than the compressive strength of the control. In Example 7, the addition of lanthanum oxide as well as sodium fluoride increased the compressive strength to 58712 (as compared to the compressive strength in Example 4 of 52452 psi, when just lanthanum oxide was added).

In Example 8, an unmodified powdered mixture of praseodymium, lanthanum, cerium and neodymium carbonate was added along with silanated titanium powder, increasing the compressive strength to 54178 psi, an 83% increase. When sodium fluoride was also added, the compressive strength increased to 56692 psi. This was not found to be significant from ANOVA (see below).

The above Examples (2-9) illustrate the effectiveness of the inventive composition as a post cement, particularly the increase in compressive strength when small amounts of a lanthanide series powder (modified or unmodified) are added to the polymer matrix.

Example 10 represents a core paste composition having a high viscosity and a compressive strength of 23154 psi. When various amounts of a powdered mixture of chemically treated praseodymium, lanthanum, cerium and neodymium carbonate were added in Examples 11-13, the compressive strength increased to 38541 psi, 39282 psi and 34632 psi respectively. These represent percent increases of 66%, 70% and 50%. When the same amount of non-chemically treated praseodymium, lanthanum, cerium and neodymium carbonate powder was added in Examples 14-16, the compressive strength increased to 43413 psi, 41536 psi and 40055 psi. These represent percent increases of 87%, 79% and 73%.

In Example 17, a small amount of untreated lanthanum oxide was added and the compressive strength increased to 45454 psi. When a similar amount of untreated praseodymium, lanthanum, cerium and neodymium carbonate powder was added (Example 18), the compressive strength was 46157 psi. The percent increase in these Examples was 96% and 99% respectively.

In Examples 19 and 20, a mixture of untreated praseodymium, lanthanum, cerium and neodymium carbonate powder and sodium fluoride was added. The compressive strength increased to 46655 psi and 45759 psi, increases approaching 100%. In Example 21, untreated titanium powder was combined with untreated praseodymium, lanthanum, cerium and neodymium carbonate powder—the compressive strength was 43592 psi. In Example 22, untreated titanium powder was combined with untreated lanthanum oxide powder—the compressive strength was 42920 psi.

Examples 23-27 illustrate the addition of chemically treated (silanated) titanium powder and a lanthanide compound to a core build-up dental composition. In Example 23, untreated lanthanum oxide was used and the compressive strength was 43296 psi. In Example 24, a powdered mixture of untreated praseodymium, lanthanum, cerium and neodymium carbonate powder was used—the compressive strength was 46204 psi. In Example 25, non-chemically treated cerium oxide powder was used and the compressive strength was 45969 psi. For Example 26, untreated neodymium oxide was used —the compressive strength was 41168 psi. In Example 27, untreated praseodymium, lanthanum, cerium and neodymium carbonate powder was again used, this time with a greater amount of chemically treated titanium powder—the compressive strength was 39904 psi.

In Examples 28-30, untreated titanium powder was added to the lanthanide composition. For Example 28, untreated cerium oxide powder was used —the compressive strength was 50503 psi. Example 29 utilized untreated praseodymium, lanthanum, cerium and neodymium carbonate powder and the compressive strength increased dramatically to 58004 psi. Example 30 also utilized untreated cerium oxide powder—this time the compressive strength was 46985 psi.

Finally, Examples 31-32 were directed to the preparation of a core build-up material in which untreated praseodymium, lanthanum, cerium and neodymium carbonate powder, titanium powder and sodium fluoride were added. Example 31 utilized silanated titanium powder; Example 32 did not. The compressive strength increased in the Examples to 47933 psi and 49297 psi respectively.

The cement and core build-up materials were analyzed separately and were not compared to one another. For the cement groups, there were eight experimental groups (including the control) (Examples 2-9). For the core build-up groups, there were 23 experimental groups (including the control) (Examples 10-32). Each of two materials was analyzed using one-way analysis of variance (ANOVA), with the dependent variable being the compressive strength. Upon finding a significant result for ANOVA, both Duncan's multiple range test (for comparing each group to one another) and Dunnett's test (for comparing each group to control) were carried out.

The mean and standard deviation for Examples 2-9 are summarized in the Table. ANOVA shows a highly significant difference between groups studied ($p < 0.0001$). Duncan's multiple range test shows that each group differed from the control. In other words, Examples 3-9 (test groups) was statistically greater than Example 2 (control). However, it is difficult to draw conclusions about which groups differ from one another. But, Dunnett's test also confirms that all groups (Examples 3-9) are different (statistically significant or greater) from the control (Example 2).

The mean and standard deviation for Examples 10-32 are also summarized in the Table. ANOVA shows a highly significant difference between groups studied ($p < 0.0001$). Duncan's multiple range test shows that each group differed from the control (Example 10) and that Example 29 (with 4% untreated praseodymium, lanthanum, cerium, neodymium carbonate powder with 2% untreated titanium powder) had the highest mean and was different from every other mean. In other words, Example 29 (was significantly greater) > Examples 11-28, 30-32 > Example 10 (Control). However, for the remaining groups, it is difficult to draw a conclusion which groups differ from one another. Dunnett's test also confirms that all groups (Examples 11-32) (statistically significant or greater) differ from the control (Example 10).

All of the statistical results above demonstrate that addition of a lanthanide species to the dental composition results in significant increases in the compressive strength.

Application of the inventive dental cement composition is as follows. Initially, the dentist or other dental personnel prepares a post-hole in the selected tooth. Post-hole preparation begins with the removal of root filling material using a reaming device. Then, a cutting drill is used to substantially create the hole—using the cutting drill, 100% of the post-hole length and 90% of the post-hole width are created. Then, a primary reamer is used to establish the entire width of the hole to make sure that it is substantially concentric.

After preparing the post-hole, the dentist selects the desired dental post, which is first temporarily inserted into the hole for trial purposes. If the dental post appears to be acceptable, the dentist will then first place a low viscosity composite dental cement composition made in accordance with the invention in the post-hole and on the post itself. Then, the post is inserted into the post-hole and threaded with light pressure. The post should seat completely with minimal resistance. After seating is completed, excess cement is removed.

In order to complete the process, it is necessary to form a core over the tooth and inserted post. This process is known as "core build up" and is carried out using a high viscosity composite dental cement composition made in accordance with the invention. The cement composition (with high viscosity) is placed in the core form and seated over the post using moderate pressure to ensure close adaptation of the composite cement to the core.

It will thus be seen that the objects set forth above, among those made apparent from the preceding description, are efficiently attained, and since certain changes may be made in carrying out the above method and in preparing the composition as set forth above without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A composite dental cement composition comprising:
    a polymer matrix in an amount between about 15 and 50 weight percent;
    a filler in an amount between about 35 and 80 weight percent; and
    a lanthanide series compound which is not modified selected from the group consisting of an oxide and a carbonate in an amount between about 1 and 20 weight percent and being a powder having a particle size of between about 5 and 10 microns.

2. The composition of claim 1, wherein the polymer matrix comprises an epoxy matrix.

3. The composition of claim 2, wherein the epoxy matrix comprises an acrylic matrix.

4. The composition of claim 3, wherein the acrylic matrix is formed from monomers of methacrylate.

5. The composition of claim 4, wherein the monomers of methacrylate are selected from the group of monomers of dimethacrylate including bisphenol A-glycidyl methacrylate, triethylene glycol dimethacrylate, tetraethylene glycol dimethacrylate, ethylene glycol dimethacrylate, diethyleneglycol dimethacrylate, butanediol dimethacrylate, isobisphenol A-glycidyl methacrylate, trimethylolpropane dimethacrylate, hexanediolethylene dimethacrylate, neopentyl glycol dimethacrylate, bisphenol A-ethoxylated dimethacrylate and bisphenol A-dimethacrylate.

6. The composition of claim 5, wherein the monomer of dimethacrylate is bisphenol A-glycidyl methacrylate in an amount between about 5 and 50 weight percent based on the total weight of the cement.

7. The composition of claim 1, wherein the filler is selected from the group including quartz, silicon dioxide, fumed silicon dioxide, aluminum dioxide, titanium dioxide, zirconium dioxide, silicas, glass, graphite fibers, boron fibers, barium glass, alumina silicates, borosilicate glass, glass powders, hydroxy apatite, wood, micas and asbestos.

8. The composition of claim 1, wherein the lanthanide series compound is present in an amount between about 2 and 10 weight percent.

9. The composition of claim 1, wherein the lanthanide series powder has a purity of at least 98%.

10. The composition of claim 1, wherein the lanthanide series compound is selected form the group consisting of europium, lanthanum, cerium, neodymium, praseodymium, yttrium, gadolinium, samarium, terbium, dysprosium, holmium, erbium, thulium, ytterbium and lutetium.

11. The composition of claim 1, wherein the lanthanide series compound comprises a powdered mixture of praseodymium, lanthanum, cerium and neodymium carbonate.

12. The composition of claim 1, further including titanium in an amount between about 2 and 5 weight percent.

13. The composition of claim 12, wherein at least some of the titanium is chemically treated.

14. The composition of claim 12, wherein at least some of the titanium is not chemically treated.

15. The composition of claim 13, wherein the chemically treated titanium is silanated titanium.

16. The composition of claim 15, wherein the silanated titanium is prepared from a silane selected from the group including gammamethacryloxy propyltrimethoxysilane, gammamethacryloxy propyltris(2-methoxyethyoxy) silane, vinyl trichlorosilane, vinyl triethyoxysilane, vinyl trimethoxysilane and vinyl triacetoxysilane.

17. The composition of claim 12, wherein the titanium is titanium powder having a particle size of between about 1 and 30 microns.

18. The composition of claim 17, wherein the titanium powder has a purity of at least a 98%.

19. The composition of claim 1, further including a fluoride in an amount between about 0.5 and 6 weight percent.

20. The composition of claim 19, wherein the fluoride is selected from the group including sodium fluoride, tin fluoride, ytterbium fluoride, an amine fluoride and an acidulated phosphate fluoride.

21. A system for preparing a composite dental cement composition comprising:
a catalyst component including a catalyst in an amount between about 0.2 and 2.0 weight percent, at least one epoxy monomer in an amount between about 15 and 50 weight percent and a filler in an amount between about 40 and 80 weight percent.
a base component comprising a base in an amount between about 0.2 and 1.5 weight percent, at least one epoxy monomer in an amount between about 20 and 50 weight percent and a filler in an amount between about 45 and 85 weight percent; and
a lanthanide series compound which is not modified selected from the group consisting of an oxide and a carbonate in an amount between about 1 and 20 weight percent based on the combined amount of catalyst, base and lanthanide compound and being a powder having a particle size of between about 5 and 10 microns.

22. The system of claim 21, wherein the catalyst of the catalyst component comprises a free radical source.

23. The system of claim 22, wherein the free radical source comprises an organic peroxide.

24. The system of claim 23, wherein the organic peroxide is selected from the group including benzoyl peroxide, acetyl peroxide, parachlorobenzoyl peroxide, cumyl peroxide, t-butyl peroxide, lauroyl peroxide, t-butyl hydroperoxide, methylethyl ketone peroxides, t-butyl peroxybenzoate, 2,5-dimethylhexane, 2,5-dihydroxy peroxide and t-cumyl hydroperoxide.

25. The system of claim 24, wherein the organic peroxide is benzoyl peroxide.

26. The system of claim 21, wherein said at least one epoxy monomer comprises at least one monomer of methacrylate.

27. The system of claim 26, wherein the at least one monomer of methacrylate is bisphenol A-glycidyl methacrylate.

28. The system of claim 21, wherein the base comprises an amine compound.

29. The system of claim 28, wherein the amine compound is selected from the group including toluidine compounds, propylamine, butyl N-butyl amine, pentylamine, hexylamine, dimethylamine, diethyleneamine, dipropylamine, di-n-butylamine, dipentylamine, trimethylamine, triethylamine, tripropylamine, tri-n-butyl amine, trimethyl amine, long chain fatty amine, tri-n-butylamine, tripentylamine, 4-methylaniline, N-N-bis-(2-hydroxyethyl)-3,5-dimethylaniline, N-methyl-N-(2-hydroxyethyl)-4-methylaniline, long chain fatty amines, diamine, trimethylene diamine, tetramethylene diamine, pentamethylene diamine and hexamethylene diamine.

30. The system of claim 29, wherein the amine compound comprises a toluidine compound.

31. The system of claim 30, wherein said toluidine compound comprises NN' dihydroxyethyl toluidine.

32. The system of claim 21, wherein the lanthanide series compound is present in an amount between about 2 and 5 weight percent.

33. The system of claim 21, wherein the lanthanide powder has a purity of at least 98%.

34. The system of claim 21, wherein the lanthanide series compound is selected form the group consisting of europium, lanthanum, cerium, neodymium, praseodymium, yttrium, gadolinium, samarium, terbium, dysprosium, holmium, erbium, thulium, ytterbium, and lutetium.

35. The system of claim 34, wherein the lanthanide series compound comprises a powdered mixture of praseodymium, lanthanum, cerium and neodymium carbonate.

36. The system of claim 21, wherein titanium is present in the system in an amount between about 2 and 5 weight percent.

37. The system of claim 36, wherein at least some of the titanium is chemically treated.

38. The system of claim 37, wherein said chemically treated titanium is silanated titanium.

39. The system of claim 38, wherein the silanated titanium is prepared from a silane selected from the group including gammamethacryloxy propyltrimethoxysilane, gammamethacryloxy propyltris(2-methoxyethyoxy) silane, vinyl trichlorosilane, vinyl triethyoxysilane, vinyl trimethoxysilane and vinyl triacetoxysilane.

40. The system of claim 36, wherein the titanium is titanium powder having a particle size of between about 1 and 30 microns.

41. The system of claim 40, wherein the titanium powder has a purity of at least 98%.

42. The system of claim 21, wherein the lanthanide series compound is added to the catalyst component prior to combining the catalyst component with the base component.

43. The system of claim 21, wherein the lanthanide series compound is added to the base component prior to combining the catalyst component with the base component.

* * * * *